United States Patent
Jiang et al.

(10) Patent No.: US 6,203,985 B1
(45) Date of Patent: *Mar. 20, 2001

(54) BIO-MOLECULE ANALYZER WITH PHOTOSENSITIVE MATERIAL AND FABRICATION

(75) Inventors: Wenbin Jiang; Barbara M. Foley, both of Phoenix; Sean Gallagher, Scottsdale; Davis H. Hartman, Chandler; Huinan Yu, Phoenix, all of AZ (US)

(73) Assignee: Motorola, Inc., Schaumburg, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/149,506

(22) Filed: Sep. 8, 1998

(51) Int. Cl.⁷ ..................................... C12Q 1/68

(52) U.S. Cl. ................ 435/6; 435/91.1; 435/287.2; 436/501; 205/91; 205/92; 205/118; 205/122; 205/340

(58) Field of Search .............. 435/6, 91.1, 287.2; 436/501; 205/91, 92, 118, 122, 340

(56) References Cited

U.S. PATENT DOCUMENTS

| | | | |
|---|---|---|---|
| 5,500,188 | 3/1996 | Hafeman et al. | 422/82.02 |
| 5,667,667 | 9/1997 | Southern | 205/687 |
| 5,810,989 | * 9/1998 | Krihak et al. | 205/91 |
| 5,985,568 | * 11/1999 | Krihak et al. | 435/6 |

FOREIGN PATENT DOCUMENTS

| | | | |
|---|---|---|---|
| 9740385 | 10/1997 | (WO) | G01N/33/543 |
| 9852042 | 11/1998 | (WO) | G01N/33/543 |

OTHER PUBLICATIONS

"The Light–Addressable Potentiometric Sensor: Principles and Biological Applications", John C. Owicki et al., Annu. Rev. Biophys. Biomol. Struct., 1994, pp. 87–113.

"Light Addressable Potentiometric Semiconductor Biosensor", H.M. McConnel et al., Extended Abstracts/Electrochemical Society, Abstract No. 1679, p. 2272.

* cited by examiner

Primary Examiner—Long V. Le
Assistant Examiner—Minh-Quan K. Pham
(74) Attorney, Agent, or Firm—William E. Koch; Eugene A. Parsons

(57) ABSTRACT

A bio-molecule analyzer includes an array of addressable light sources, a photoconductive layer of material having a layer of electrically conductive material on a surface thereof mounted on the array of addressable light sources, and a plurality of test sites on an opposing surface of the photoconductive layer of material defined by the plurality of light sources. A solution containing a plurality of bio-molecules is positioned in electrical contact with the plurality of test sites. An electrical potential is connected between the solution and the layer of electrically conductive material, whereby the array of addressable light sources emit beams of light through a plurality of portions of the photoconductive layer of material to define the test sites and complete electrical circuits between the layer of electrically conductive material and the solution.

10 Claims, 2 Drawing Sheets

BIO-MOLECULE ANALYZER WITH PHOTOSENSITIVE MATERIAL AND FABRICATION

BACKGROUND OF THE INVENTION

1. Field of the Invention

This invention relates to analysis of molecular samples. More particularly, the present invention relates to fabrication of molecular analyzers and analysis of bio-molecule samples.

2. Prior Art

Identification of molecular structure has become very important in many industries. In particular, biological molecules such as nucleic acids and proteins are analyzed to form the basis of clinical diagnostic assays. The procedures utilized often involve large numbers of repetitive steps which consume large amounts of time. With the advent of large projects such as the human genome project, faster and less complex techniques are required.

Simpler and quicker analysis of molecules has been provided by the development of devices often referred to as bio chips, which are arrays of test sites formed on a substrate. Each of the plurality of test sites includes probes therein to bond with target molecules from samples applied to the device. The binding of a molecule to a probe is noted, thereby identifying the molecule.

While increasing the speed and efficiency of analyzing samples, the arrays of test sites must still immobilize specific bio-molecules on a solid surface to act as probes. Conventionally, placing bio-molecules as probes on specific test sites is time consuming, expensive, often lacks the desired accuracy and does not meet the desired size constraints. Placement of bio-molecules for probes is conventionally accomplished by in-situ synthesis using photolithography, which is very labor intensive with unsatisfactory accuracy, mechanical spotting, which is a slow process with the smallest test site size limited by the nature of the process, or chemical ink jetting, having an inaccuracy similar to in-situ synthesis and test site size limits similar to mechanical spotting.

Furthermore, once fabrication has been completed, a method for the detection of the bonding of the probe with a target molecule must be provided. There are many techniques for determining which test sites have molecules bonded to them including autoradiography, optical detection (fluorescence) and electronic detection. The use of monolithic devices with an array of test sites generally require externally accessible terminals for each test site. As the number of test sites in an array is increased, the complexity of providing and making contact with the terminals for each test site becomes increasingly difficult and burdensome.

It would be highly advantageous, therefore, to remedy the foregoing and other deficiencies inherent in the prior art.

Accordingly, it is an object of the present invention to provide a new and improved apparatus for analyzing molecules and method for fabrication and use thereof.

Another object of the present invention is to provide a method and apparatus for analyzing molecules using wireless contacts for a spatially addressable array of test sites.

And another object of the present invention is to provide a method and apparatus for analyzing molecules which is fast and efficient.

A further object of the present invention is to provide a method and apparatus for analyzing molecules wherein the light source array is used to fabricate the test sites and is therefore self aligned with the test sites for use as the excitation source in optical detection.

Still another object of the present invention is to provide a method and apparatus which can include more test sites than prior art methods using wire connections in the same area.

SUMMARY OF THE INVENTION

Briefly, to achieve the desired objects of the instant invention, in accordance with a preferred embodiment thereof, provided is a method of fabricating a bio-molecule analyzer including the steps of providing a photoconductive layer of material having a layer of electrically conductive material on a first surface thereof and a test site on an opposing second surface thereof. A solution containing a plurality of probe molecules is placed in electrical contact with the test site and an electrical potential is connected between the solution and the layer of electrically conductive material. A beam of light is directed through a portion of the photoconductive layer of material to complete an electrical circuit between the layer of electrically conductive material and the solution through the portion of the photoconductive layer and the test site. In this manner, probe molecules in the solution are attracted to and bound to the test site, which is coupled into the electrical circuit by the beam of light.

Also provided is a bio-molecule analyzer including a photoconductive layer of material, having a layer of electrically conductive material on a first surface thereof, mounted on an array of addressable light sources. A plurality of test sites on an opposing second surface of the photoconductive layer of material are defined by the plurality of light sources. A solution containing a plurality of bio-molecules is received by the analyzer in electrical contact with the plurality of test sites. An electrical potential is connected between the solution and the layer of electrically conductive material. The array of addressable light sources emit beams of light through a plurality of portions of the photoconductive layer of material to define the test sites and complete electrical circuits between the layer of electrically conductive material and the solution through the plurality of portions of the photoconductive layer and the plurality of test sites.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
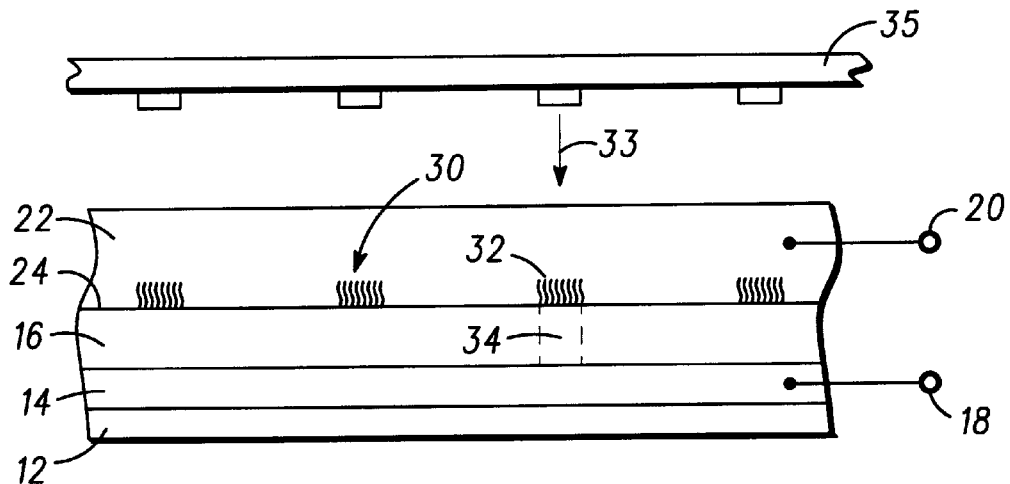
FIG. 1 is a sectional view of a bio-molecule analyzer according to the present invention.

Turning now to the drawings in which like reference characters indicate corresponding elements throughout the several views, attention is first directed to FIG. 1 which illustrates a bio-molecule analyzer generally designated 10. Bio-molecule analyzer 10 includes a substrate 12 preferably fabricated of silicon, glass, plastic, etc., a thin conductive layer 14 formed on substrate 12, and a photoconductive layer 16 formed on thin conductive layer 14. Thin conductive layer 14 can be any conductive material such as gold, platinum etc., and can be indium tin oxide (ITO) or other optically transparent conductors for reasons which will become apparent from the subsequent description. Photoconductive layer 16 is a material such as amorphous silicon, CdS, CdSe, various photoconductive polymers, etc. which becomes conductive when subjected to light.

Still referring to FIG. 1, a lead 18 is coupled to conductive layer 14 and a lead 20 is coupled to a solution 22 positioned in electrical contact with a surface 24 of photoconductive layer 16 opposite to conductive layer 14. While not specifically shown, it will be understood that solution 22 is in electrical contact only with surface 24 and not with conductive layer 14. A potential is applied across leads 18 and 20 and thus between solution 22 and conductive layer 14.

Still referring to FIG. 1, a beam or beams of light 33 are directed through a portion 34 of photoconductive layer 16 defining a test site 30 (preferably one test site for each beam). In this embodiment, test sites 30 are formed into an array, with each test site 30 being an area of surface 24 substantially coextensive with a corresponding portion 34. The beam or beams of light 33 complete an electrical circuit between conductive layer 14 and solution 22 through portion 34 of photoconductive layer 16. This is accomplished by beam of light 33 temporarily converting portion 34 of photoconductive layer 16 to a conducting medium.

Solution 22 contains ionic probe molecule to be bound to test sites 30. By completing the circuit, the ionic probe molecules in solution 22 are attracted to and concentrate proximate surface 24 at a selected one or ones of test sites 30. It will be understood that any method of controllably illuminating a selected portion 34 of photoconductive layer 16 can be used, such as a masked light source, the use of a laser or diode array 35 or similar device instead of or in combination with a mask which permits passage of light in only the desired locations. Array 35 can be a one dimensional or two dimensional array of light sources which are individually addressable, i.e. one or more light sources can be activated as desired.

The array of test sites 30 (micro-locations) defined on surface 24 have groups of probes 32 coupled thereto. Each test site 30 contains a plurality of probes 32 which are capable of binding to specific molecular structures. The molecular structure can comprise, for example, biopolymers such as polynucleotides, protein, DNA, RNA, cells, enzymes, antibodies, antigens, etc. In the case of DNA or RNA testing, probes 32 can comprise, for example, oligonucleotides. All probes 32 at a given test site 30 are identical. Probes in respective test sites differ in sequence for simultaneous detection of a plurality of different target molecules within a single array. Each test site 30 is individually addressable by array 35 to provide the ability to attract ionic probe molecules from solution 22 to selected test site(s) 30 in order to fabricate an array of test sites each for detecting different molecules or sequences.

Figure 2:
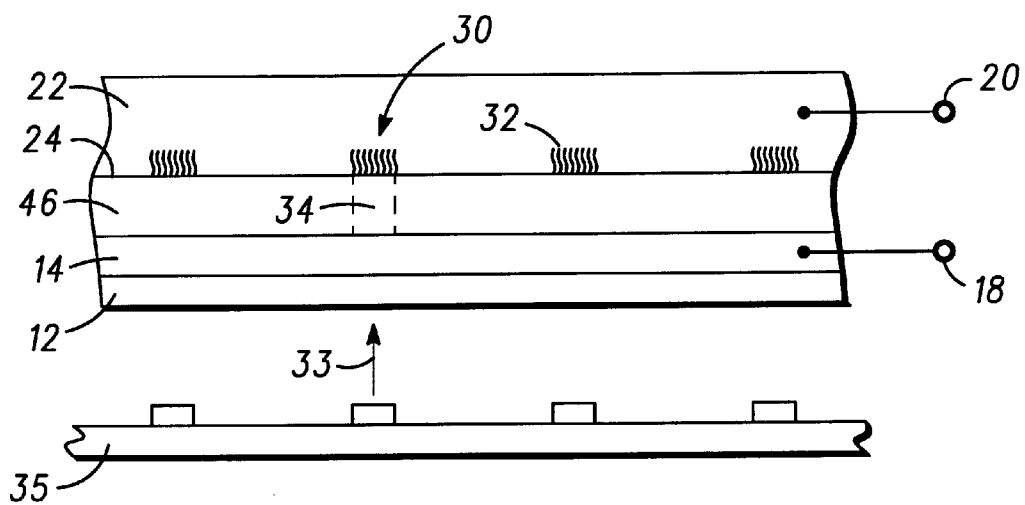
FIG. 2 is a sectional view illustrating another embodiment of a bio-molecule analyzer according to the present invention.

In the previous description, light 33 is directed at photoconductive layer 16 through solution 22. With reference to FIG. 2, the same elements are illustrated, but light 33 is directed through substrate 12 and thin conductive layer 14. In this case, substrate 12 must be formed of a material transparent to light 33 such as glass, plastic, etc., and thin conductive layer 14 must be a transparent conductor such as indium tin oxide (ITO), various thin metals or other optically transparent materials. It will be understood that when the term transparent is used throughout the text, it refers to a material's ability to transmit light being used to transform photoconductive layer 16.

A specific process of fabricating a bio-molecule analyzer (e.g. analyzer 10) includes providing a first solution, containing a plurality of first probe molecules, in electrical contact with the plurality of test sites 30. An electrical potential is applied between the first solution and the layer of electrically conductive material 14 by means of leads 18 and 20. A beam of light 33 is directed through a first portion 34 of the photoconductive layer 16 to complete an electrical circuit between the layer of electrically conductive material 14 and the first solution through the first portion 34 of the photoconductive layer 16 and a first test site 30 of the array of test sites. Completing the electrical circuit causes first probe molecules in the first solution to be attracted to a first test site 30. While probe molecules 32 can be bound to test sites 30 in any manner, in a preferred embodiment, the probe molecules 32 include a monomer, such as pyrrole, which polymerizes with material at surface 24. The circuit is then broken by deactivating the light source and the first solution is removed leaving a test site with a plurality of identical probes bound thereto.

The fabrication process continues by providing a second solution, containing a plurality of second probe molecules, in electrical contact with the plurality of test sites 30. An electrical potential is applied between the second solution and the layer of electrically conductive material 14 by means of leads 18 and 20. A beam of light 33 is directed through a second portion 34 of the photoconductive layer 16 to complete an electrical circuit between the layer of electrically conductive material 14 and the second solution through the second portion 34 of the photoconductive layer 16 and a second test site 30 of the array of test sites. Completing the electrical circuit causes second probe molecules in the second solution to be attracted to a second test site 30 where they are bound as described above.

This process is repeated as many times as needed to produce a bio-molecule analyzer having a desired number or array of different test sites each with different probe molecules. In this fashion, an analyzer having a one or two dimensional array of test sites can be easily fashioned with a reduction in labor intensity greater accuracy, quicker processing and the ability to build very small test sites.

To analyze a sample, a solution containing the sample bio-molecules is introduced into analyzer 10. The solution is positioned in contact with the plurality of probe molecules 32 at each of the plurality of test sites 30 so as to allow interaction between the sample bio-molecules and the pluralities of probe molecules. The solution is removed and the array of light sources is employed as excitation sources for optical detection of the binding events between the sample molecules and the corresponding probe molecules, i.e. hybridization, etc. Thus, the interaction between matching sample bio-molecules and probe molecules is easily detected. It is anticipated that other detection techniques such as electrical detection can also be employed with the present invention. In the case of electrical detection, for example, each portion 34 of layer 16 is sequentially illuminated by sequentially activating the array of light sources 35, one at a time. The binding events are determined by, for example, sensing changes of resistivity, capacity, or measuring the induced current between leads 18 and 20, as is known in the art. Thus, individual leads are not required for each test site 30, which is very difficult to achieve and grows in difficulty with increased numbers of test sites, but can instead be easily incorporated into array of light sources 35. Since individual leads are not required arrays of test sites can be made smaller, denser and include an overall larger number of test sites, equivalent to the density of the fabricating beams.

Figure 3:
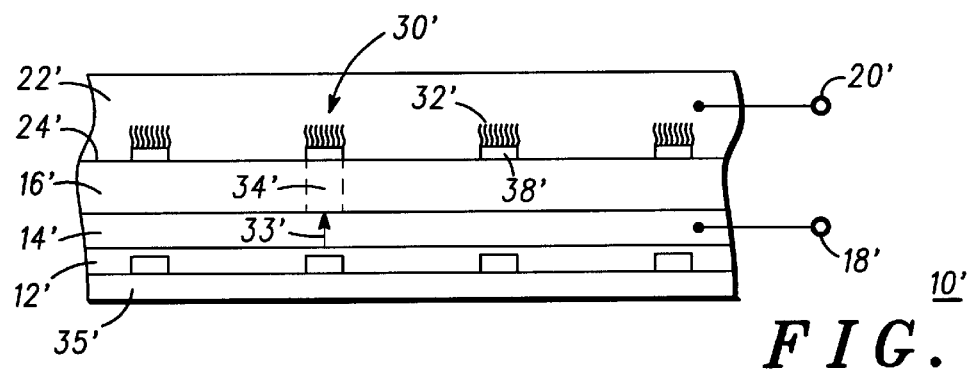
FIG. 3 is a sectional view illustrating yet another embodiment of a bio-molecule analyzer according to the present invention.

Turning to FIG. 3, another embodiment of an analyzer 10' in accordance with the present invention is illustrated. Analyzer 10' is a modification of analyzer 10 of FIGS. 1 and 2 in which similar elements are designated with similar numbers and have a prime added to indicate a different embodiment. Bio-molecule analyzer 10' includes an array of light sources 35' fabricated on a supporting substrate, such as a semiconductor chip or the like. A thin planarizing and insulating layer 12' preferably fabricated of plastic, spin-on-glass, etc., is deposited over the array of light sources 35' and a thin conductive layer 14' is formed on layer 12'. A photoconductive layer 16' with an upper surface 24' is formed on thin conductive layer 14'. Thin conductive layer 14' can be any conductive material such as gold, platinum etc., and can be indium tin oxide (ITO) or other optically transparent conductors for reasons which will become apparent from the subsequent description. Photoconductive layer 16' is a material such as amorphous silicon, CdS, CdSe, various photoconductive polymers, etc. which becomes conductive when subjected to light.

Still referring to FIG. 3, a lead 18' is coupled to conductive layer 14' and a lead 20' is coupled to a solution 22' positioned in electrical contact with a surface 24' of photoconductive layer 16' opposite to conductive layer 14'. While not specifically shown, it will be understood that solution 22' is in electrical contact only with surface 24' and not with conductive layer 14'. A potential is applied across leads 18' and 20' and thus between solution 22' and conductive layer 14'. As described above in connection with FIGS. 1 and 2, individual circuits are established between solution 22' and conductive layer 14' by employing light beams 33' from the array of light sources 35'.

By integrating the array of light sources 35' directly into analyzer 10', processing is simplified, and array of light sources 35' is used to both facilitate bonding of probe molecules to specific test sites, and also since the beam of light defines the test site, it is self aligned for use as a light source for the excitation beam in optical detection.

Figure 4:
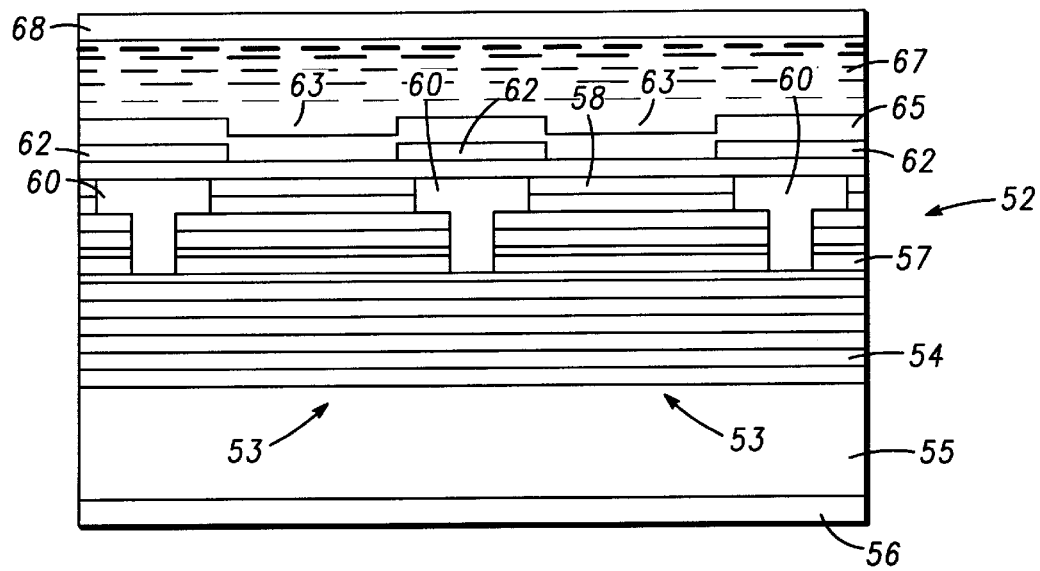
FIGS. 4 and 5 are simplified sectional views illustrating sequential steps in the fabrication of another bio-molecule analyzer according to the present invention.

Turning now to FIG. 4, a first step in the fabrication of an analyzer 50 is illustrated. A vertical cavity surface emitting laser (VCSEL) array 52 is first made using conventional fabrication processes. VCSEL array 52 includes a plurality of VCSELs 53 arranged in a one or two dimensional array. Each VCSEL includes a first mirror stack 54 positioned on a substrate 55. Substrate 55 has one contact 56 of each VCSEL 53 deposited on the opposing surface thereof. An active area 57 is positioned on first mirror stack 54 and a second mirror stack 58 is positioned on active area 57. Implants 60 are introduced into second mirror stack 58 to limit current flow and lasing to a specific area within each laser 53. Planar proton implant VCSELs are preferred due to the fewer number of process steps involved. An upper contact 62 is formed on second mirror stack 58 defining a light emission aperture, which in this embodiment corresponds to a test site 63. The wavelength of the light produced can be adjusted to a desired value such that it properly functions as an excitation light source for optical detection. As is known in the art, the wavelength of the emitted light can be adjusted by the materials used (for example in active layer 57) and the thickness of the layers in the mirror stacks.

After VCSEL array 52 has been fabricated, a photoconductive layer 65, preferably amorphous silicon or polysilicon material, is deposited onto the upper surface of VCSEL array 52 as a photoconductive switch for fabrication and/or analysis. Depending on the nature of the fabrication, the next step can be in either wafer format or chip format. Wafer level fabrication is the most desired process from lowering the fabrication cost stand point. Certain applications require custom analyzers, such analyzers can be fabricated using diced VCSEL array chips.

Figure 5:
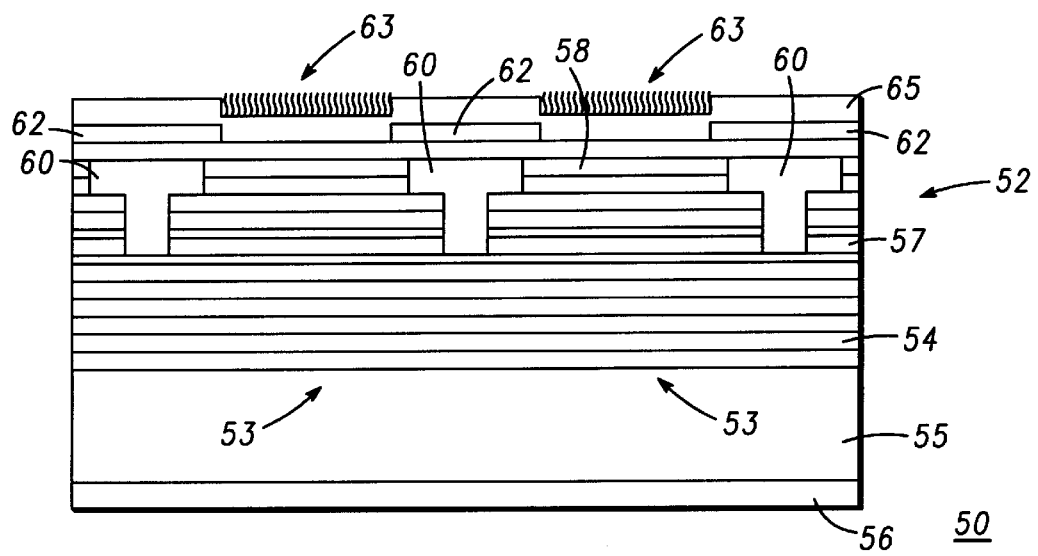

The fabrication process includes providing a solution 67, containing a plurality of probe molecules, in electrical contact with the plurality of test sites 63. A contact 68 is positioned in solution 67 such that a potential can be applied between solution 67 and upper contacts 62 of VCSELs 52. The probe molecules in solution 67 are attracted to a specific test site 63 by activating a selected VCSEL 53 of array 52 the aperture of which corresponds to the desired test site 63. Upper contact 62 of the selected VCSEL 53 is positively biased and contact 56 is grounded or biased at a lower potential. Contact 68 in solution 67 is biased at a lower potential than upper contact 62 of selected VCSEL 53 to provide a potential difference therebetween. When emitted light from selected VCSEL 53 is absorbed by photoconductive layer 65 at corresponding test site 63, the material becomes electrically conductive (i.e. the photoswitch is on) and current flows between upper contact 62 and contact 68 in solution. The current flow assists the probes in solution 67 to collect at test site 63 as shown in FIG. 5. To provide different probe molecules for each different test site, solutions containing different probe molecules are interchanged and selected test sites are charged by activating the corresponding VCSEL.

As with the embodiment illustrated in FIG. 3, by integrating VCSEL array 52 directly into analyzer 50, processing is greatly simplified, and VCSEL array 52 can be used to both facilitate bonding of probe molecules to specific test sites, and also since the apertures of the VCSELs define the test sites, it is self aligned for use as a light source for the excitation beam in optical detection.

Thus, provided is a new and improved method and apparatus for analyzing molecules using wireless contacts for a spatially addressable array of test sites which increases the speed and efficiency of both analysis and fabrication and increases the number of test sites possible in a given area.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice same, the invention claimed is:

1. A method of fabricating a bio-molecule analyzer comprising the steps of:
providing a photoconductive layer of material having a layer of electrically conductive material on a first surface thereof and a plurality of test sites on an opposing second surface thereof;
providing a solution containing a plurality of probe molecules in electrical contact with the plurality of test sites;
connecting an electrical potential between the solution and the layer of electrically conductive material; and directing beams of light through a plurality of portions of the photoconductive layer of material to complete an electrical circuit between the layer of electrically conductive material and the solution through the portions of the photoconductive layer and the plurality of test sites, the step of directing the beams of light includes providing an array of light sources, whereby probe molecules in the solution are attracted to and bound to the plurality of test sites, which are coupled into the electrical circuit by the beams of light.

2. A method as claimed in claim 1 wherein the step of directing a beam of light includes providing a light source selected from a group consisting of organic electroluminescent devices, light emitting diodes, lasers, vertical cavity surface emitting lasers, and a masked light source.

3. A method as claimed in claim 2 further including the step of forming the photoconductive layer of material having the layer of electrically conductive material on the first surface thereof and the test site on the opposing second surface thereof on the light source.

4. A method as claimed in claim 3 wherein the step of providing the light source includes providing a light source with two terminals, one of which is the electrically conductive material.

5. A method as claimed in claim 1 wherein the photoconductive layer includes one of amorphous silicon, CdS, CdSe, amorphous silicon carbide, and photoconductive polymer.

6. A method of fabricating a bio-molecule analyzer comprising the steps of:

providing a photoconductive layer of material having a layer of electrically conductive material on a first surface thereof and a plurality of test sites on an opposing second surface thereof;

providing a first solution containing a plurality of first probe molecules in electrical contact with the test site;

connecting an electrical potential between the first solution and the layer of electrically conductive material;

directing a first beam of light through a first portion of the photoconductive layer of material to complete an electrical circuit between the layer of electrically conductive material and the first solution through the first portion of the photoconductive layer and the first test site of the plurality of test sites, whereby first probe molecules in the first solution are attracted to and bound to the first test site, which is coupled into the electrical circuit by the first beam of light;

removing the first solution;

providing a second solution containing a plurality of second probe molecules in electrical contact with the plurality of test sites;

connecting an electrical potential between the second solution and the layer of electrically conductive material; and directing a second beam of light through a second portion of the photoconductive layer of material to complete an electrical circuit between the layer of electrically conductive material and the second solution through the second portion of the photoconductive layer and a second test site of the plurality of test sites, the steps of directing the first beam of light and the second beam of light including providing an array of light sources, whereby second probe molecules in the second solution are attracted to and bound to the second test site, which is coupled into the electrical circuit by the second beam of light.

7. A method as claimed in claim 6 wherein the steps of directing a first and a second beam of light include providing an array of light sources selected from a group consisting of organic electroluminescent devices, light emitting diodes, lasers and vertical cavity surface emitting lasers.

8. A method as claimed in claim 7 further including the step of forming on the array of light sources the photoconductive layer of material having the layer of electrically conductive material on the first surface thereof and the plurality of test sites on the opposing second surface thereof each light source of the array of light sources corresponding to one of the plurality of test sites.

9. A method as claimed in claim 8 wherein the step of providing the array of light sources includes providing an array of light sources with two terminals, one of which is the electrically conductive material.

10. A method as claimed in claim 8 wherein the step of providing the array of light sources includes providing an addressable array of light sources.

\* \* \* \* \*